(12) United States Patent
Matsushita et al.

(10) Patent No.: US 12,042,579 B2
(45) Date of Patent: Jul. 23, 2024

(54) SELF-EXPANDING STENT AND MANUFACTURING METHOD THEREFOR

(71) Applicant: TERUMO KABUSHIKI KAISHA, Tokyo (JP)

(72) Inventors: Shuhei Matsushita, Hadano (JP); Kazuyoshi Tani, Kawasaki (JP); Atsunori Yoshida, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 945 days.

(21) Appl. No.: 17/017,346

(22) Filed: Sep. 10, 2020

(65) Prior Publication Data

US 2020/0405920 A1  Dec. 31, 2020

Related U.S. Application Data

(63) Continuation of application No. PCT/JP2019/002966, filed on Jan. 29, 2019.

(30) Foreign Application Priority Data

Mar. 15, 2018 (JP) ................................. 2018-048377

(51) Int. Cl.
*A61L 31/04* (2006.01)
*A61L 31/14* (2006.01)
(Continued)

(52) U.S. Cl.
CPC ........... *A61L 31/041* (2013.01); *A61L 31/148* (2013.01); *C08G 63/912* (2013.01); *A61F 2/89* (2013.01);
(Continued)

(58) Field of Classification Search
None
See application file for complete search history.

(56) References Cited

U.S. PATENT DOCUMENTS 8,679,396 B2 * 3/2014 Kleiner ................... A61L 31/14
264/494
2010/0262223 A1  10/2010 Kleiner
(Continued)

FOREIGN PATENT DOCUMENTS

AU  2007204617 A1 *  7/2007
JP  2013526649 A  6/2013
(Continued)

OTHER PUBLICATIONS

International Search Report (PCT/ISA/210) mailed on Apr. 9, 2019, by the Japanese Patent Office as the International Searching Authority for International Application No. PCT/JP2019/002966.
(Continued)

*Primary Examiner* — Tae H Yoon
(74) *Attorney, Agent, or Firm* — BUCHANAN INGERSOLL & ROONEY PC

(57) ABSTRACT

A self-expandable stent has sufficient radial force, has good bending properties, and recovers the shape for the diameter thereof to return from a diameter in a contracted state to a diameter before contraction around a body temperature (37° C.). The self-expandable stent includes a crosslinked polymer containing a constitutional unit (A) obtained from a monomer that constitutes a rigid biodegradable polymer when homopolymerized and a constitutional unit (B) obtained from a crosslinking agent, in which a content of the constitutional unit (B) is 15% by weight to 35% by weight with respect to a content of the constitutional unit (A).

16 Claims, 3 Drawing Sheets

(51) Int. Cl.
  *C08G 63/91* (2006.01)
  *A61F 2/89* (2013.01)
(52) U.S. Cl.
  CPC ...... *A61L 2400/16* (2013.01); *C08G 2230/00* (2013.01)

(56) References Cited

U.S. PATENT DOCUMENTS

2013/0123384 A1 5/2013 Grijpma
2014/0025161 A1 1/2014 Stankus
2020/0108182 A1 4/2020 Matsushita

FOREIGN PATENT DOCUMENTS

| JP | 2015527920 A | 9/2015 |
|---|---|---|
| WO | 2008051254 A1 | 5/2008 |
| WO | WO 2014/057349 A2 * | 4/2014 |
| WO | 2019013101 A1 | 1/2019 |

OTHER PUBLICATIONS

Written Opinion (PCT/ISA/237) mailed on Apr. 9, 2019, by the Japanese Patent Office as the International Searching Authority for International Application No. PCT/JP2019/002966.

An English Translation of the International Search Report (Form PCT/ISA/210) and the Written Opinion of the International Searching Authority (Form PCT/ISA/237) issued on Apr. 9, 2019, by the Japanese Patent Office in corresponding International Application No. PCT/JP2019/002966. (7 pages).

* cited by examiner

[FIG. 1A]
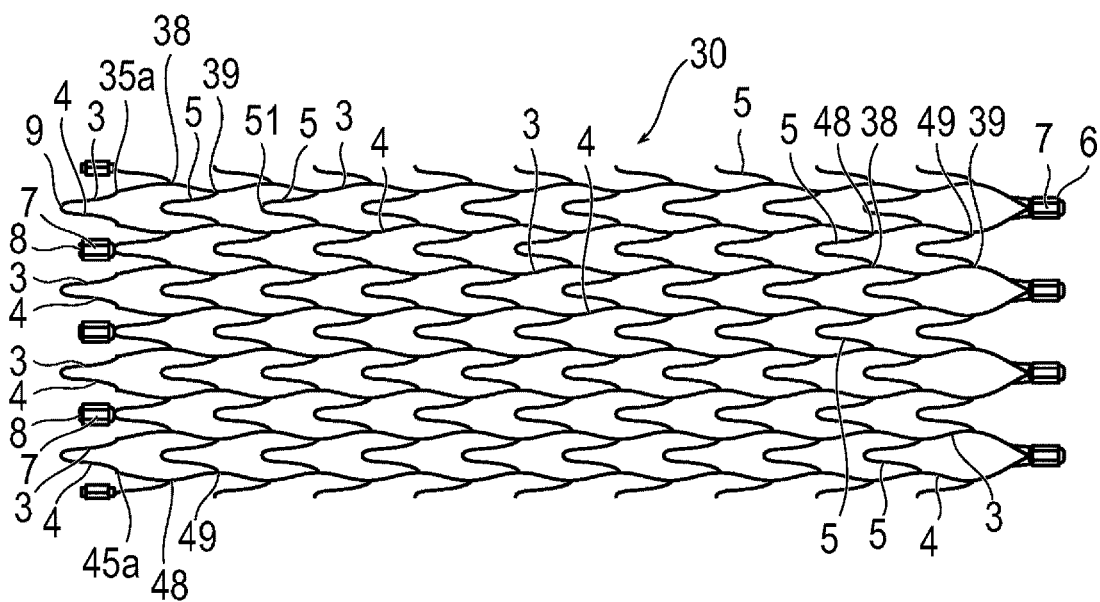
[FIG. 1B]
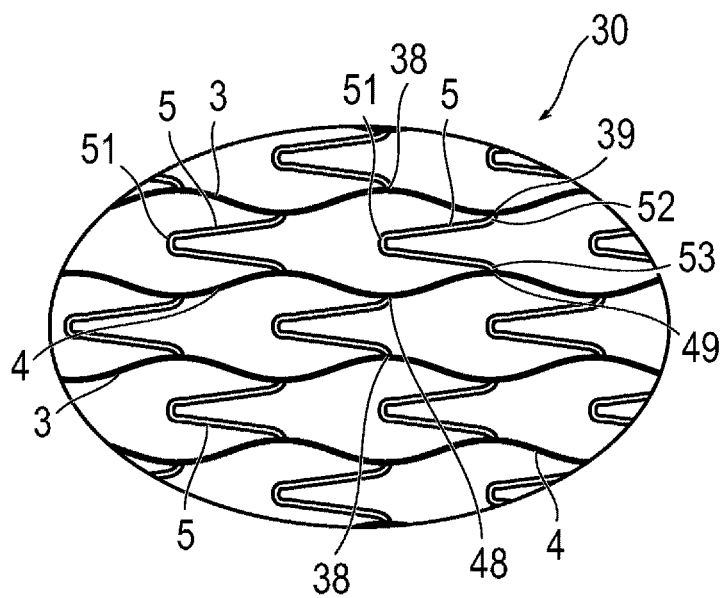

[FIG. 2]
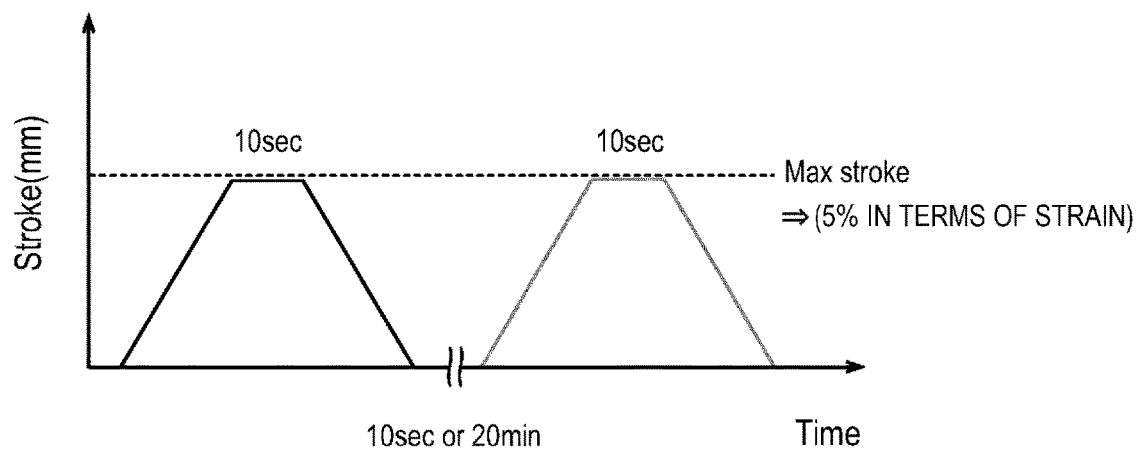
[FIG. 3]
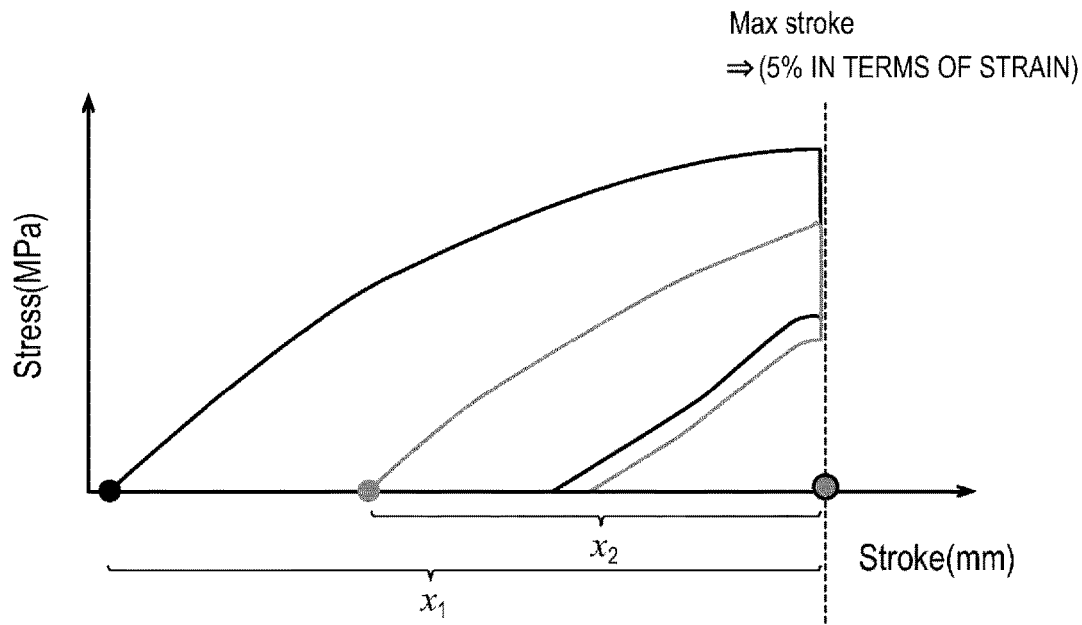

[FIG. 4]
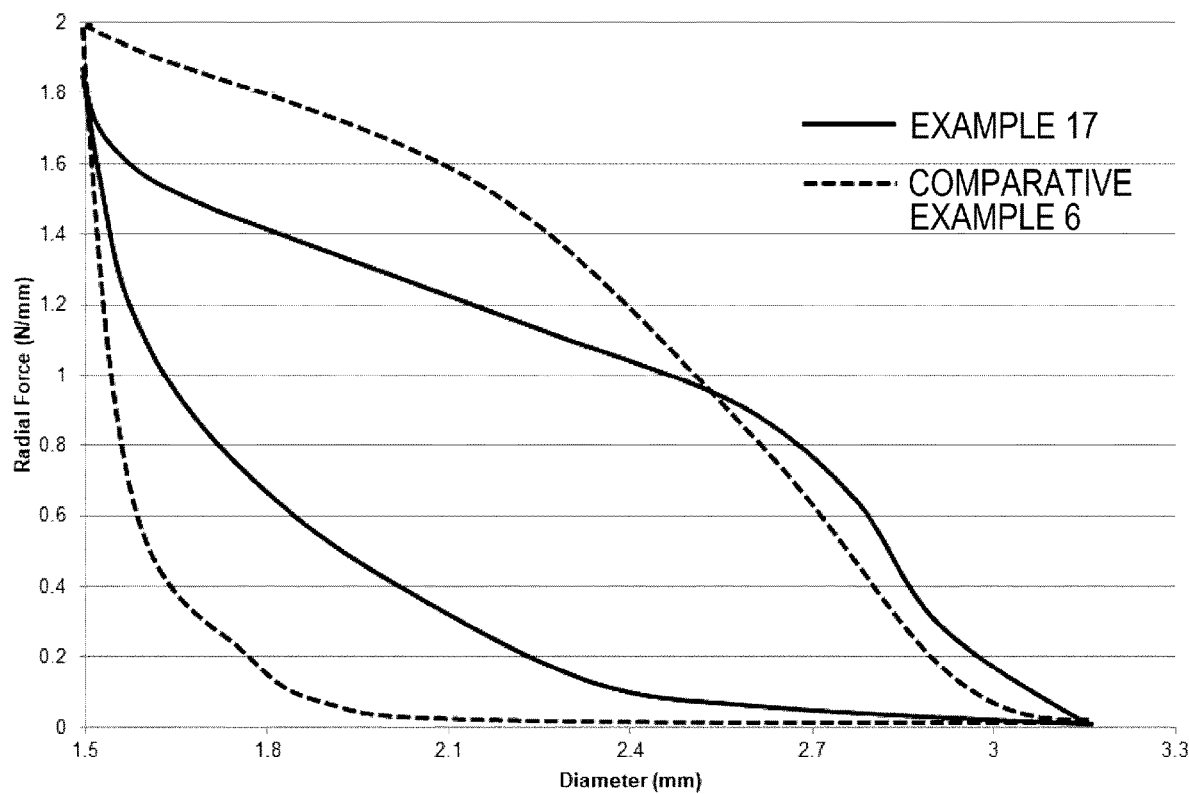

SELF-EXPANDING STENT AND MANUFACTURING METHOD THEREFOR

CROSS-REFERENCES TO RELATED APPLICATIONS

This application is a continuation of International Patent Application No. PCT/JP2019/002966 filed on Jan. 29, 2019, which claims priority to Japanese Patent Application No. 2018-048377 filed on Mar. 15, 2018, the entire contents of both of which are incorporated herein by reference.

TECHNICAL FIELD

The present disclosure relates to a self-expandable stent and a method for producing the same.

BACKGROUND DISCUSSION

A stent is a medical device that can be used to expand a stenosed or obstructed site to thereby secure a lumen, in order to treat various diseases caused by stenosis or obstruction of a lumen such as a blood vessel. In recent years, acute myocardial infarction (AMI) has been also treated using a stent. In a treatment of AMI (which is a thrombotic lesion) using a stent, incomplete stent apposition (ISA) of the stent to a vascular wall is likely to occur due to thrombolysis after the stent is indwelled.

Examples of a stent include a balloon-expandable stent that is expanded with a balloon to which the stent is mounted and a self-expandable stent that expands by itself by removal of a member which suppresses the expansion thereof from the outside.

The self-expandable stent can be stored in a contracted state in a delivery system such as a sheath, and when the self-expandable stent reaches an indwelling site, the self-expandable stent can be released from restriction to thereby self-expand. Therefore, the use of a self-expandable stent does not require the balloon expansion operation that is performed in the case where a balloon-expandable stent is used. A self-expandable stent made of a super-elastic alloy such as a nickel-titanium alloy is commercially available in Europe. Short-term incomplete stent apposition in AMI treatment has been dramatically improved by a treatment with such a self-expandable stent.

The use of a super-elastic alloy such as nickel-titanium as a material for forming a stent can provide a strong radial force (expansion retention force in a radial direction). The super-elastic alloy is effective in that a vascular wall maintains a given diameter over a treatment period. However, since a strong radial force is applied to the vascular wall for a long time after the treatment period has elapsed, there is a case where the self-expandable stent made of a super-elastic alloy is inferior to the balloon-expandable stent in major adverse cardiac events (MACE), for example, target lesion revascularization (TLR) of medium to long-term clinical outcomes.

In view of the above situation, a stent made of a biodegradable material has been developed. Since the biodegradable material is gradually degraded in a living body, it is anticipated that the radial force of the stent decreases over time to improve the medium to long-term clinical outcomes (particularly for TLR).

As such a biodegradable stent, JP-T-2015-527920 (corresponding to WO 2014/018123) discloses a stent produced from a shape-memory random copolymer composed of poly (L-lactide) (PLLA) and a rubber-like polymer.

In addition, the specification of U.S. Patent Application Publication No. 2010/0262223 discloses a method for producing a stent, the method including crosslinking a biodegradable polymer by a crosslinking agent to form a base material.

SUMMARY

However, the stent disclosed in JP-T-2015-527920 (corresponding to WO 2014/018123) is required to be expanded from a crimped state (contracted state) to an expanded state with a balloon catheter. Furthermore, [0119] of JP-T-2015-527920 (corresponding to WO 2014/018123) states that a stent fabricated using a resin composed of 90:10 (by mole) of polylactic acid and polycaprolactone recoils inwardly for 60 minutes after expansion and then recoils outwardly (recovers the shape) over several days. When the shape recovery is slow as described above, incomplete stent apposition of the stent is likely to occur. It is also considered that the incomplete stent apposition of the stent may lead to an onset of stent thrombosis and may lead to movement of the stent caused by blood flow in some cases. Therefore, the self-expandable stent requires a rapid shape recovery to cause the diameter thereof to return early from a diameter in a contracted state to a diameter before contraction.

In contrast, as disclosed in [0049] of JP-T-2015-527920 (corresponding to WO 2014/018123), it is considered that in a copolymer of PLLA and a rubber-like polymer, the blending amount of the rubber-like polymer is increased to improve elastic properties of the polymer and reduce the inward recoil. However, when the amount of the rubber-like polymer is merely increased in the resin, the stent does not have enough strength in the radial direction to support a stenosed artery.

In addition, in the specification of U.S. Patent Application Publication No. 2010/0262223, a tendency of a stent to undergo self-expansion is disclosed, but the speed of shape recovery to cause the stent to expand outwardly from a contracted state around the body temperature (37° C.) is not studied. Furthermore, in the specification of U.S. Patent Application Publication No. 2010/0262223, the production of a self-crosslinking-type polymer formed from L-lactide and α-allyl-σ-valerolactone or a self-crosslinking-type polymer formed from L-lactide-α and α-diallyl-σ-valerolactone is merely discussed, and the characteristics thereof are not specifically studied.

Furthermore, when a stent is contracted in diameter from an expanded state to a crimped state (contracted state), a local stress of approximately 10% is applied to the vicinity of turned-back portions (apexes of the zigzag) of a stent strut in a tensile direction and a compression direction, so that a strain is generated. Therefore, resistance to the generated strain is also desirable.

Therefore, according to an exemplary aspect, provided is a biodegradable self-expandable stent that, while maintaining a sufficient radial force, has high strain resistance and exhibits rapid shape recovery where the self-expandable stent expands outwardly when released from restriction in a contracted state around the body temperature (37° C.).

According to an aspect of the present disclosure, there is provided a self-expandable stent having a crosslinked polymer containing a constitutional unit (A) obtained from a monomer that constitutes a rigid biodegradable polymer when homopolymerized and a constitutional unit (B) obtained from a crosslinking agent, in which a content of the constitutional unit (B) is 15% by weight to 35% by weight with respect to a content of the constitutional unit (A).

BRIEF DESCRIPTION OF THE DRAWINGS

FIG. 1A and FIG. 1B illustrate a stent according to an exemplary embodiment. FIG. 1A is a development view of the stent, and FIG. 1B is a partial enlargement view of FIG. 1A.

FIG. 2 is a graph showing the stroke displacement (stroke, the length of displacement) over time in a tensile test for explaining a recovery rate, according to an exemplary aspect.

FIG. 3 is a stress-stroke displacement chart in a tensile test for explaining a recovery rate, according to an exemplary aspect.

FIG. 4 is a graph showing measurement results of the radial force of stents in Example 17 and Comparative Example 6, according to an exemplary aspect.

DETAILED DESCRIPTION

Hereinafter, embodiments of the present disclosure will be described. Note that the present disclosure is not limited to the following embodiments. In this specification, "X to Y" that indicates a range means "X or more and Y or less" and unless otherwise specified, operations and the measurement of physical properties or the like are carried out under conditions of room temperature (20 to 25° C.) and a relative humidity of 40 to 50% RH.

According to an exemplary embodiment of the present disclosure, there is provided a self-expandable stent having a crosslinked polymer containing a constitutional unit (A) obtained from a monomer that constitutes a rigid biodegradable polymer when homopolymerized and a constitutional unit (B) obtained from a crosslinking agent, in which a content of the constitutional unit (B) obtained from the crosslinking agent is 15% by weight to 35% by weight with respect to a content of the constitutional unit (A) obtained from the monomer that constitutes the rigid biodegradable polymer when homopolymerized.

According to an exemplary embodiment of the self-expandable stent, it is possible to provide a biodegradable self-expandable stent that, while maintaining a sufficient radial force, has a high speed of shape recovery when the stent is released from restriction in a contracted state and has sufficient resistance to a local stress to a stent strut, the local stress being generated when the stent is contracted in diameter from an expanded state to a crimped state (contracted state).

Hereinafter, the constitutional unit (A) obtained from the monomer that constitutes a rigid biodegradable polymer when homopolymerized is also referred to as the constitutional unit (A) and the constitutional unit (B) obtained from the crosslinking agent is also referred to as the constitutional unit (B).

For example, the crosslinked polymer has a structure where a polymer containing the constitutional unit (A) is crosslinked with the constitutional unit (B) obtained from the crosslinking agent.

Since the constitutional unit (A) is rigid, the polymer thereof (i.e., without the constitutional unit (B)) has rigidity around the body temperature. However, since the polymer containing the constitutional unit (A) without the constitutional unit (B) has almost no elasticity, the speed of shape recovery to return from a decreased diameter during insertion to the diameter before contraction is slow. In addition, such a stent formed from the polymer containing the constitutional unit (A) without the constitutional unit (B) has no sufficient resistance to a local stress to a stent strut (refer to data for the recovery rates after 10 seconds and 20 minutes and the strain-resistance properties in Comparative Example 1 discussed below). As described above, it is difficult for the biodegradable self-expandable stent to have sufficient strain characteristics and shape recoverability while maintaining rigidity.

In an exemplary embodiment, since the polymer is crosslinked with the crosslinking agent, particularly, the content of the constitutional unit (B) is 15% by weight to 35% by weight with respect to the content of the constitutional unit (A), despite having high rigidity, the self-expandable stent can exhibit superior strain characteristics and shape recoverability. The reason is considered that when the content of the constitutional unit (B) is present in an amount of 15% by weight or more, the crystallinity of the polymer containing the constitutional unit (A) is decreased to cause the polymer to be easily deformed, so that the polymer exhibits improved strain resistance and has shape-memory properties. In addition, when the content of the constitutional unit (B) is 35% by weight or less, since the brittleness of the resin caused by the addition of the crosslinking agent is not revealed, high strain resistance is maintained.

For example, the stent can self-expand quickly (for example, within 10 seconds) from a diameter during insertion (decreased diameter in a state where the stent is incorporated into a delivery system, for example, 1.5 mm) to an indwell diameter (diameter immediately after the stent is indwelled in the body, for example, 3.0 mm). For example, the stent can self-expand early (for example, within 20 minutes) from the indwell diameter to an initial diameter (natural diameter in a state where the stent is not restricted before incorporated into the delivery system, for example, 4.0 mm). For example, since the stent can exhibit sufficient strength in a radial direction, the expansion of a wall of a lumen such as a blood vessel in the radial direction is maintained, and since the stent has biodegradability, the strength of the stent in the radial direction decreases in the process of healing. For example, according to the self-expandable stent of an exemplary embodiment, the incomplete stent apposition of the stent is reduced and furthermore, the radial force is reduced as the polymer degrades over time to thereby improve medium to long-term clinical outcomes (for example, for TLR).

Hereinafter, a stent of an exemplary embodiment will be described with reference to the drawings. The dimensional ratios in the drawings are exaggerated for the sake of description and may be different from the actual ratios. In the description of the specification, the longitudinal direction (rightward and leftward direction in FIG. 1A) of the stent is referred to as an axial direction.

Exemplary components of the stent will be described. Examples of the shape and structure of the stent include the shape and structure of the stent illustrated in FIG. 7 or 8 of WO 2011/034009. A configuration of a stent 10 described by illustration is one example, and the stent of the present disclosure is not limited to the shape and the structure (for example, the arrangement and the design of a strut) to be described here.

As illustrated in FIGS. 1A and 1B, the stent 10 according to an exemplary embodiment includes a stent base body (stent main body portion) 30, and has a substantially cylindrical contour having a given length in the axial direction as a whole. For example, the stent 10 is indwelled in a lumen (for example, blood vessel, bile duct, trachea, esophagus, other gastrointestinal tracts, and urethra) in a living body and is used to widen the lumen to thereby treat a stenosed or obstructed site. For example, the stent 10 is a self-expandable stent which self-expands such that the stent base body 30 returns to a pre-memorized shape having a given large diameter after the start of indwelling. For example, the stent 10 is a biodegradable stent which is degraded and absorbed in the living body. For example, a strut forming the stent base body 30 of the stent 10 has a biodegradable crosslinked polymer. For example, the crosslinked polymer is degraded in the living body, for example, by hydrolysis.

For example, the stent base body 30 includes a plurality of wave struts 3 and 4 that extend in the axial direction from one end to the other end of the stent base body 30 and are arranged in a circumferential direction of the stent, and a plurality of connection struts 5 that connect the wave struts 3 and 4 adjacent to each other. For example, the wave struts 3 and 4 adjacent to each other include a plurality of closer portions and distant portions, and the connection strut 5 connects the closer portions of the wave struts 3 and 4 adjacent to each other and includes a bent portion 51, which extends in the axial direction of the stent, in a central portion of the connection strut 5. For example, the bent portion 51 of the connection strut 5 is a free end extending toward a distal end direction of the stent 10. For example, the first wave strut 3 and the second wave strut 4 have a sine wave shape.

For example, in the stent base body 30, the first wave strut 3 and the second wave strut 4 have substantially the same wavelength and substantially the same amplitude, and the second wave strut 4 is shifted by approximately half wavelength in the axial direction of the stent with respect to the first wave strut 3.

For example, as illustrated in FIG. 1B, in the first wave strut 3 and the second wave strut 4 adjacent to each other, a top point 38 or a bottom point 39 of the first wave strut 3 and a bottom point 48 or a top point 49 of the second wave strut 4 substantially face each other to form the closer portion and the distant portion. For example, in the stent base body 30, the wave struts 3 and 4 all have the same length except both ends thereof.

For example, in the stent base body 30, both end portions 52 and 53 of the connection strut 5, the both end portions 52 and 53 being connected to the wave struts 3 and 4, are slightly-bent portions which are curved outside the connection strut 5. For example, the connection strut 5 is connected to the top point 38 or the bottom point 39 of the wave strut 3 and the bottom point 48 or the top point 49 of the wave strut 4 in the slightly-bent portions.

For example, in a distal portion of the stent base body 30, a bent portion 9 formed by the joining of distal portions of the first wave strut 3 and the second wave strut 4 and a bulging portion 8 provided in the bent portion 51 of the connection strut 5 are alternately provided in the circumferential direction. For example, a radiopaque marker 7 to be described later is attached to the bulging portion 8. In addition, the bent portion 9 is positioned closer to a distal side of the stent than the bulging portion 8. For example, as described above, the radiopaque marker on the distal side is positioned slightly closer to inside than the end portion of the stent. For example, since the strut extends further outside than the marker, the strut can securely cover a lesion area.

For example, in the stent base body 30, slightly-bent portions 35*a* and 45*a* which are bent inwardly of the bent portion 9 are provided closer to a proximal side by a given distance than the bent portion 9 formed by the joining of the distal portions of the first wave strut 3 and the second wave strut 4 to thereby increase the expansion retention force of the bent portion 9 which is a long free end.

For example, in the stent base body 30, in proximal portions of the stent, all the proximal portions of the first wave strut 3 and the second wave strut 4 are joined to a joint portion 6. For example, except the joint portion 6, the stent base body 30 includes no free end facing a proximal end direction of the stent. In other words, for example, all the bent portions face the distal end direction of the stent. For example, when a sheath is moved toward the distal side relative to the stent, since there is no free end toward the sheath (stent storage member), it is possible to store the stent into the sheath (stent storage member) again without the stent being hooked by the sheath.

For example, the radiopaque marker 7 is attached to the joint portion 6. For example, the joint portion 6 includes two frame portions that extend in parallel to each other toward an end portion direction while being distant from each other by a given distance, and the radiopaque marker 7 covers substantially the entirety or a part of the two frame portions. For example, the radiopaque marker 7 has a thin rectangular parallelepiped shape, store the two frame portions therein, and is fixed to the two frame portions by a recess in a central portion of the radiopaque marker 7. For example, one material (single element) or two or more materials (alloy) selected from a group of elements consisting of, for example, iridium, platinum, gold, rhenium, tungsten, palladium, rhodium, tantalum, silver, ruthenium, and hafnium may be suitably used as the material forming the radiopaque marker.

Examples of the stent according to the present disclosure include stents and stent grafts.

Any suitable thickness can be adopted as the thickness of the stent. For example, the thickness of the stent is approximately from 50 to 500 µm, and according to the relationship between the supportability and the degradation time, the thickness can be approximately from 60 to 300 µm, for example, approximately from 70 to 200 µm. Since the stent base body according to an exemplary embodiment has superior dynamic properties (for example, expansion retention force), the thickness of the stent can be reduced.

The size of the stent can be appropriately adjusted according to the purpose and the function thereof. For example, the outer diameter (the diameter) of the stent after expansion can be approximately from 1 to 40 mm, for example, approximately from 1.5 to 10 mm, for example, approximately from 2 to 5 mm.

For example, the length of the stent is not specifically limited and can be appropriately selected depending on a disease to be treated. For example, the length can be approximately from 5 to 300 mm, for example, approximately from 10 to 50 mm.

In an exemplary embodiment, the stent base body 30 has the crosslinked polymer. For example, the crosslinked polymer contains a constitutional unit (A) obtained from a monomer that constitutes a rigid biodegradable polymer when homopolymerized and a constitutional unit (B) obtained from a crosslinking agent. For example, the crosslinked polymer has a structure where polymer chains are crosslinked by the constitutional unit (B). For example, the crosslinked polymer is obtained by polymerizing a polymer containing the constitutional unit (A) and a crosslinking agent of 15% by weight to 35% by weight with respect to the content of the constitutional unit (A).

Hereinafter, the polymer containing the constitutional unit (A) may be simply referred to as a "polymer" in some cases.

Regarding the rigid biodegradable polymer, a rigid polymer refers to a polymer that when obtained by homopolymerizing a monomer, the resulting homopolymer has a glass transition temperature (Tg) in a range of 40° C. or higher. The polymer having a glass transition temperature of 40° C. or higher has rigidity at the body temperature (around 37° C.). For example, the polymer formed from a monomer that constitutes a rigid biodegradable polymer when homopolymerized can maintain a force in a radial direction even when the stent is indwelled in a lumen.

A value measured by using Diamond DSC, which is manufactured by Perkin Elmer, according to JIS K7121: 2012 (Measurement methods for transition temperatures of plastics) is employed as the glass transition temperature.

In addition, in this specification, "biodegradable" means that in a biodegradability test described in Examples, an elongation at fracture after a hydrolysis test is 90% or less (lower limit: 0%) of an elongation at fracture before the hydrolysis test.

For example, from the viewpoint of biodegradability, the polymer contains at least one of lactic acid and glycolic acid as the monomer that constitutes a rigid biodegradable polymer when homopolymerized. Specific examples of the monomer include L-lactic acid (Tg of poly L-lactic acid (PLLA): 60° C.), D-lactic acid (Tg of poly D-lactic acid (PDLA): 60° C.), glycolic acid (Tg of polyglycolic acid (PGA): 45° C., and the like. One of the monomers may be used alone or two or more thereof may be used in combination. For example, L-lactic acid and glycolic acid may be used in combination and L-lactic acid and D-lactic acid may be used in combination.

For example, among the above monomers, the monomer that constitutes a rigid biodegradable polymer when homopolymerized can be lactic acid or lactic acid and glycolic acid because of superior biodegradability and mechanical strength, for example, lactic acid, for example, L-lactic acid because of superior shape recoverability (for example, the recovery rate after 10 seconds in Examples is high).

For example, when the monomer is lactic acid, since a high molecular weight polymer cannot be obtained by a direct polycondensation method, the monomer can be polymerized by ring-opening polymerization using lactide, as desired, in the presence of a catalyst. Examples of lactide include L-lactide which is a cyclic dimer of L-lactic acid, D-lactide which is a cyclic dimer of D-lactic acid, meso-lactide which is a cyclic dimer of D-lactic acid and L-lactic acid, and DL-lactide which is a racemic mixture of D-lactide and L-lactide. For example, similarly, also with glycolic acid, a high molecular weight polymer cannot be obtained by a direct polycondensation method, and thus ring-opening polymerization of glycolide can be used.

The polymer containing the constitutional unit (A) may contain a constitutional unit obtained from another monomer that can be copolymerized with a monomer that constitutes a rigid biodegradable polymer when homopolymerized. In view of the effects of the present disclosure, it is exemplary that the polymer contain almost no such another monomer or the another monomer be absent from the polymer. For example, such another monomer can be contained in an amount of 5% by weight or less, for example, 2% by weight or less, for example, is not substantially contained with respect to the amount of all the constitutional units constituting the polymer.

"Being not substantially contained" means that the content is 0.01% by weight or less (lower limit: 0% by weight). According to an exemplary embodiment, the polymer consists substantially of the constitutional unit (A) obtained from a monomer that constitutes a rigid biodegradable polymer when homopolymerized. Here, consisting substantially of the constitutional unit (A) obtained from a monomer that constitutes a rigid biodegradable polymer when homopolymerized means that the content of the constitutional unit (A) obtained from the monomer is 99.9% or 99.99% by weight or more (upper limit: 100% by weight). For example, the polymer consists only of the constitutional unit (A) obtained from a monomer that constitutes a rigid biodegradable polymer when homopolymerized.

For example, it is exemplary that the polymer containing the constitutional unit (A) contains almost no constitutional unit obtained from another monomer that can be copolymerized with a monomer that constitutes a rigid biodegradable polymer when homopolymerized. For this reason, it is exemplary that the polymer before crosslinking has a high Young's modulus. For example, the Young's modulus of the polymer before crosslinking is preferably 500 N/mm$^2$ or more, for example, 750 N/mm$^2$ or more. According to an exemplary embodiment, the crosslinked polymer is obtained by polymerizing the crosslinking agent with the polymer containing the constitutional unit (A) obtained from a monomer that constitutes a rigid biodegradable polymer when homopolymerized, the content of the crosslinking agent is 15% by weight to 35% by weight with respect to the content of the constitutional unit (A) obtained from the monomer that constitutes a rigid biodegradable polymer when homopolymerized, and the Young's modulus of the polymer containing the constitutional unit (A) is 500 N/mm$^2$ or more. A value measured by a method to be described in Examples is employed as the Young's modulus.

Regarding a method for producing the polymer containing the constitutional unit (A), the polymer can be produced with any suitable method. For example, when the constitutional unit (A) is lactic acid, a polymerization reaction can be carried out using lactide, which is a cyclic dimer of lactic acid, as a raw material in the presence of a metal catalyst. Examples of the metal catalyst include tin chloride, tin octylate, zinc chloride, zinc acetate, lead oxide, lead carbonate, titanium chloride, alkoxy titanium, germanium oxide, zirconium oxide, and the like. For example, the polymerization reaction may be carried out in the presence of an organic solvent. For example, a polymerization initiator may be used in the polymerization reaction. Examples of lactide include L-lactide which is a cyclic dimer of L-lactic acid, D-lactide which is a cyclic dimer of D-lactic acid, meso-lactide which is a cyclic dimer of D-lactic acid and L-lactic acid, and DL-lactide which is a racemic mixture of D-lactide and L-lactide. In the present disclosure, any lactide may be used. For example, a plurality of sets of the above monomers can be combined to synthesize the polymer.

For example, from the viewpoint of improvement in mechanical strength and biodegradability, the weight average molecular weight of the polymer containing the constitutional unit (A) can be from 100,000 to 1,000,000, for example, 150,000 to 800,000, for example, 150,000 to 600,000. The weight average molecular weight in this specification is a value measured under the following measurement conditions by gel permeation chromatography (GPC) using polystyrenes which are standard substances.

(Measurement Conditions of Molecular Weight)

Apparatus: semi-micro GPC system LC-20AD (manufactured by Shimadzu Corporation)

Detector: Shodex (registered trademark) RI-104 (manufactured by Showa Denko K.K.)

Column: Shodex (registered trademark) GPC LF-404 (manufactured by Showa Denko K.K.)

Column temperature: 40° C.

Mobile phase solvent: CHCl$_3$

Flow rate: 0.15 mL/min

Injection: 20 μL

Sample preparation: 2 mL of the mobile phase solvent is added to 6 mg of a sample to be measured to dissolve the sample, followed by filtering with a 0.45-μm PTFE membrane filter.

As the polymer containing the constitutional unit (A), a commercial product may be used, and examples of the commercial product include BioDegmer (registered trademark) PLLA (manufactured by BMG Inc.); and Resomer (registered trademark) L206S, Resomer (registered trademark) RG756S, Resomer (registered trademark) RG858S, and Resomer (registered trademark) LG824S (all manufactured by EVONIK Industries AG).

For example, the constitutional unit (B) is obtained from the crosslinking agent.

It is exemplary that the crosslinking agent in the constitutional unit (B) is a monomer having two or more polymerizable unsaturated bonds. Examples of the polymerizable unsaturated bond include an acryloyl group (CH$_2$=CH—CO—), a methacryloyl group (CH$_2$=C(CH$_3$)—CO—), and a vinyl group (—CH=CH—).

Specific examples of the crosslinking agent include bifunctional (meth)acrylates such as diethylene glycol diacrylate, 1,4-butanediol diacrylate, 1,3-butylene glycol diacrylate, dicyclopentanyl diacrylate, glycerol diacrylate, 1,6-hexanediol diacrylate, neopentyl glycol diacrylate, tetraethylene glycol diacrylate, ethylene glycol dimethacrylate, polyethylene glycol dimethacrylate, diethylene glycol dimethacrylate, triethylene glycol dimethacrylate, 1,4-butanediol dimethacrylate, 1,3-butylene glycol dimethacrylate, dicyclopentanyl dimethacrylate, glycerol dimethacrylate, 1,6-hexanediol dimethacrylate, neopentyl glycol dimethacrylate, tetraethylene glycol dimethacrylate, 1,9-nonanediol dimethacrylate, and 1,10-decanediol dimethacrylate; trifunctional (meth)acrylates such as trimethylolpropane triacrylate, pentaerythritol triacrylate, tetramethylolmethane acrylate, trimethylolpropane trimethacrylate, and pentaerythritol trimethacrylate; tetra- or higher-functional (meth)acrylates such as pentaerythritol tetraacrylate, ditrimethylolpropane tetraacrylate, dipentaerythritol penta/hexa-acrylate, dipentaerythritol hexaacrylate, dipentaerythritol monohydroxypentaacrylate, pentaerythritol tetramethacrylate, ditrimethylolpropane tetramethacrylate, dipentaerythritol penta/hexa-methacrylate, dipentaerythritol hexamethacrylate, and dipentaerythritol monohydroxypentamethacrylate; acrylamide-based compounds such as N, N'-methylenebisacrylamide, N, N'-methylenebismethacrylamide, N, N'-ethylenebisacrylamide, N, N'-ethylenebismethacrylamide, N, N'-hexamethylenebisacrylamide, N, N'-hexamethylenebismethacrylamide, N, N'-benzylidene bisacrylamide, and N, N'-bis(acrylamidemethylene)urea; carboxylic acid allyl esters such as trimellitic acid triallyl ester, pyromellitic acid triallyl ester, and diallyl oxalate; cyanuric acid or isocyanuric acid allyl esters such as triallyl cyanurate and triallyl isocyanurate; maleimide compounds such as N-phenylmaleimide and N,N'-m-phenylenebismaleimide; compounds having two or more triple bonds such as dipropargyl phthalate and dipropargyl maleate; and divinylbenzene. For example, one of the crosslinking agents may be used alone or two or more thereof may be used in combination.

The crosslinking agent can be a monomer having an acryloyl group (CH$_2$=CH—CO—) or a methacryloyl group (CH$_2$=C(CH$_3$)—CO—). The crosslinking agent can be a multifunctional (meth)acrylate because of superior shape recoverability. For example, because of superior shape recoverability, the multifunctional (meth)acrylate as the crosslinking agent can be a tetra- or higher-functional (meth)acrylate, for example, a tetra- to hexa-functional (meth)acrylate.

Among the above crosslinking agents, it is exemplary that the crosslinking agent is pentaerythritol tetraacrylate, ditrimethylolpropane tetraacrylate, dipentaerythritol penta/hexa-acrylate, dipentaerythritol hexaacrylate, dipentaerythritol monohydroxypentaacrylate, pentaerythritol tetramethacrylate, ditrimethylolpropane tetramethacrylate, dipentaerythritol penta/hexa-methacrylate, dipentaerythritol hexamethacrylate, and dipentaerythritol monohydroxypentamethacrylate, for example, pentaerythritol tetraacrylate and/or dipentaerythritol penta/hexa-acrylate.

For example, the absolute value of the difference between the solubility parameter value of the crosslinking agent and the solubility parameter value of the constitutional unit (A) can be 5 (J/cm$^3$)$^{1/2}$ or less. According to an exemplary embodiment, the crosslinked polymer is obtained by polymerizing the crosslinking agent with the polymer containing the constitutional unit (A) obtained from a monomer that constitutes a rigid biodegradable polymer when homopolymerized, and the absolute value of the difference between the solubility parameter value of the crosslinking agent and the solubility parameter value of the monomer that constitutes a rigid biodegradable polymer when homopolymerized (hereinafter, also referred to as a solubility parameter difference) is 5 (J/cm$^3$)$^{1/2}$ or less. For example, since the solubility parameter difference is 5 (J/cm$^3$)$^{1/2}$ or less, when the stent is released from restriction in a contracted state, the stent expands outwardly to rapidly recover the shape in the body temperature (37° C.). For example, the crosslinking reaction proceeds uniformly since the crosslinking agent has a high compatibility with the polymer. For example, the solubility parameter difference can be 2 (J/cm$^3$)$^{1/2}$ or less, for example, 1.5 (J/cm$^3$)$^{1/2}$ or less. Note that the lower limit of the solubility parameter difference is zero.

"The solubility parameter (SP value)" refers to an SP value determined by a formula based on the Fedors method. Specifically, the SP value can be calculated by the following formula (1) as described in Robert F Fedor, Poly Eng Sci 1974; 14(2): 147-154.

$$SP=(\Delta Ev/V)^{1/2} \quad (1)$$

In the formula, ΔEv represents the molar cohesive energy (the energy of vaporization at a given temperature), and V represents the molar volume. Note that in this application, "a given temperature" means a measurement value at 25° C.

One of the crosslinking agents may be used alone or two or more thereof may be used in combination.

For example, the content of the constitutional unit (B) is 15% by weight to 35% by weight with respect to the content of the constitutional unit (A). When the content of the constitutional unit (B) is less than 15% by weight with respect to the content of the constitutional unit (A), the shape recoverability is significantly reduced (Comparative Example 2 to be described later). On the other hand, when the content of the constitutional unit (B) exceeds 35% by weight in the crosslinked polymer, the resin is brittle and the strain resistance is significantly reduced (Comparative Examples 3 and 4 to be described later).

For example, when the stent is released from restriction in a contracted state, the stent expands outwardly to more rapidly recover the shape in the body temperature (37° C.) and therefore, the content of the constitutional unit (B) can exceed 20% by weight and is 35% by weight or less with respect to the content of the constitutional unit (A), for example, 25% by weight to 35% by weight.

For example, the content of the constitutional unit (B) coincides with the amount of addition of the crosslinking agent in a production stage. For example, the content of the constitutional unit (B) can be found out by degrading the stent material to the monomer constitutional units using hydrolysis and quantifying the monomer containing the constitutional unit (B) by HPLC.

For example, the crosslinked polymer can be obtained by polymerizing the polymer and the crosslinking agent of 15% by weight to 35% by weight with respect to the content of the constitutional unit (A). A method for producing the crosslinked polymer will be described later.

A crosslink means a chemical bond that links one polymer chain to another polymer chain. As a non-limiting example, a C—H bond in a copolymer is cut by irradiation with ultraviolet rays or the like to generate a free radical site, and the free radical site reacts with an unsaturated bonding site in a crosslinking agent to thereby form a structure where the copolymer is crosslinked with the crosslinking agent.

The crosslinked polymer may contain an additional biodegradable constitutional unit in addition to the constitutional units (A) and (B). Examples of a compound used to introduce the additional biodegradable constitutional unit into the polymer include hydroxycarboxylic acids, dicarboxylic acids, polyhydric alcohols, cyclic depsipeptide, and the like. In addition, the content rate of the additional biodegradable constitutional unit can be 0 to 10% by mole, for example, 0 to 5% by mole with respect to the content of all the constitutional units of the crosslinked polymer.

The Young's modulus of the crosslinked polymer can be 500 N/mm$^2$ or more. For example, when the Young's modulus is within such a range, the radial force is increased and the mechanical strength is secured. The Young's modulus of the crosslinked polymer can be 600 N/mm$^2$ or more, for example, 800 N/mm$^2$ or more, for example, 1,000 N/mm$^2$ or more. For example, a higher Young's modulus of the crosslinked polymer can be exemplary, and thus the upper limit thereof is not specifically limited; however, the Young's modulus can be generally 3,000 N/mm$^2$ or less. The Young's modulus of the crosslinked polymer can be controlled by the addition of a photopolymerization initiator during crosslinking or the like. For example, since the addition of the photopolymerization initiator during crosslinking improves polymerization efficiency, the Young's modulus tends to be increased.

A value measured by a method to be described later in Examples is employed as the Young's modulus of the crosslinked polymer.

The recovery rate of the crosslinked polymer after 10 seconds can be 65% or more. For example, since the recovery rate after 10 seconds is 65% or more, the diameter of the stent immediately returns from a decreased diameter during insertion to a diameter before contraction, and expansion by a balloon catheter is not required, so that incomplete stent apposition is reduced. The recovery rate after 10 seconds can be 70% or more, for example, 75% or more. For example, the upper limit of the recovery rate after 10 seconds is 100%; however, the recovery rate can be generally 95% or less. The recovery rate after 10 seconds can be controlled by the amount of addition of the crosslinking agent and the type of the crosslinking agent (combination of the crosslinking agent and the polymer). For example, the larger the amount of addition of the crosslinking agent, the higher the recovery rate after 10 seconds tends to be.

For example, the recovery rate of the crosslinked polymer after 20 minutes can be 80% or more, for example, 90% or more. For example, since the recovery rate after 20 minutes is 80% or more, the stent can substantially return from the decreased diameter during insertion to the diameter before contraction, so that incomplete stent apposition is reduced. For example, the upper limit of the recovery rate after 20 minutes is 100%.

A value measured by a method to be described later in Examples is employed as the recovery rate of the crosslinked polymer after 10 seconds or the recovery rate thereof after 20 minutes.

In an exemplary self-expandable stent described in this disclosure, the recovery rate of the resin (for example, crosslinked polymer) forming the stent base body after 20 minutes is 70% or more.

According to an exemplary embodiment, the Young's modulus of the crosslinked polymer is 500 N/mm$^2$ or more and the recovery rate after 10 seconds is 65% or more. According to another exemplary embodiment, the Young's modulus of the crosslinked polymer is 600 N/mm$^2$ or more and the recovery rate after 10 seconds is 65% or more. According to still another exemplary embodiment, the Young's modulus of the crosslinked polymer is 800 N/mm$^2$ or more and the recovery rate after 10 seconds is 65% or more.

For example, the gel fraction of the crosslinked polymer can be 50% or more, for example, 70% or more. Since the gel fraction is within the above range, the crosslinking proceeds sufficiently, so that a desired effect can be obtained. For example, the degree of crosslinking can be found out from the gel fraction. For example, the upper limit of the gel fraction is not specifically limited; however, the gel fraction can be 100% or less. A value measured by a method to be described later in Examples is employed as the gel fraction.

Alternatively, the degree of crosslinking (for example, crosslinking density) in the crosslinked polymer can be also measured by a method for tracing the degree of decrease in the peak of the heat of fusion by DSC.

For example, the Martens hardness of the stent in a loading-unloading test using a nanoindenter (hereinafter, also referred to simply as Martens hardness) can be 50 N/mm$^2$ or more. For example, since the Martens hardness is 50 N/mm$^2$ or more, the radial force is increased and the mechanical strength is secured. The Martens hardness can be 50 N/mm$^2$ or more, for example, 100 N/mm$^2$ or more. For example, a higher Martens hardness of the stent can be exemplary, and thus the upper limit thereof is not specifically limited; however, the Martens hardness can be generally 300 N/mm$^2$ or less. For example, the Martens hardness of the stent can be controlled by the addition of a photopolymerization initiator during crosslinking or the like. For example, since the addition of the photopolymerization initiator during crosslinking improves polymerization efficiency, the Martens hardness tends to be increased.

It is exemplary that the crosslinked polymer has lower crystallinity (higher amorphousness) in view of the ease of hydrolysis, namely, biodegradability. For example, an operation of increasing the crystallinity, such as annealing, is not particularly required in the production process.

An exemplary embodiment of the present disclosure is a method for producing a self-expandable stent, the method including polymerizing a polymer containing a constitutional unit (A) obtained from a monomer that constitutes a rigid biodegradable polymer when homopolymerized and a crosslinking agent of 15% by weight to 35% by weight with respect to the content of the constitutional unit (A) to obtain a crosslinked polymer; and producing the stent using the crosslinked polymer.

For example, the polymer containing the constitutional unit (A) obtained from a monomer that constitutes a rigid biodegradable polymer when homopolymerized is as described above.

For exam pleaddition, specific examples of the crosslinking agent are as described above.

For example, the polymerization of the polymer and the crosslinking agent is not specifically limited, but may be any mode such as solution polymerization or bulk polymerization. For example, the solvent used in the solution polymerization may be a solvent that can dissolve the polymer and the crosslinking agent, and examples thereof include chloroform, 1,1,1,3,3,3-hexafluoro-2-propanol, N—N-dimethylformamide, and the like.

For example, the method of polymerization can be photopolymerization since unsaturated bonds can be easily activated. Examples of light (active radiations) used in the method include ionizing radiations such as electron beams, α-rays, β-rays, and γ-rays; and ultraviolet rays. It is exemplary that since the production facility is simple and production is easy, the polymerization of the polymer and the crosslinking agent is carried out under irradiation with ultraviolet rays among the above rays. The wavelength of ultraviolet rays can be 200 to 400 nm. In addition, the amount of irradiation with ultraviolet rays is appropriately set such that the polymerization is properly carried out. The amount of irradiation can be, for example, 500 to 20,000 mJ/cm$^2$, for example, 1,000 to 5,000 mJ/cm$^2$.

For example, when the polymerization is carried out under irradiation with ultraviolet rays, it is exemplary that the polymerizing is carried out in the presence of a photopolymerization initiator. For example, since the addition of the photopolymerization initiator improves polymerization efficiency, the Young's modulus and the Martens hardness are increased. The photopolymerization initiator may be selected according to the wavelength of irradiating ultraviolet rays, and may be any one of alkylphenone compounds such as benzyldimethylketal, α-hydroxyalkylphenone and α-aminoalkylphenone; acylphosphine oxide compounds such as MAPO and BAPO; and an oxime ester compound. From the viewpoint of polymerization efficiency, the photopolymerization initiator can be an alkylphenone compound, for example, α-hydroxyalkylphenone.

Specific examples of the photopolymerization initiator include α-hydroxyalkylphenones such as 2-hydroxy-1-[4-(2-hydroxyethoxy)phenyl]-2-methyl-1-propanone, 2-hydroxy-2-methyl-1-phenyl-1-propanone, and 1-hydroxy-cyclohexyl-phenyl-ketone; α-aminoalkylphenones such as 2-methyl-1-[4-methylthiophenyl]-2-morpholinopropan-1-one, 2-benzyl-2-dimethylamino-1-(4-morpholinophenyl)butanone-1, and 2-dimethylamino-2-(4-methylbenzyl)-1-(4-morpholin-4-ylphenyl)butan-1-one; and acylphosphineoxide compounds such as diphenyl(2,4,6-trimethylbenzoyl)-phosphineoxide and phenylbis(2,4,6-trimethylbenzoyl).

As the photopolymerization initiator, a commercial product may be used, and examples of the commercial product include Irgacure 2959, 184, 1173, 907, 369E, 379EG, TPO, 819 (all manufactured by BASF), and the like.

One of the photopolymerization initiators may be used alone or two or more thereof may be used in combination.

The amount of the photopolymerization initiator can be 1 to 20% by weight with respect to the amount of the crosslinking agent, for example, 2 to 15% by weight.

The timing of light irradiation is not specifically limited, and after a mixture containing the copolymer and the crosslinking agent is molded into a tube shape by extrusion, injection molding, or the like, the light irradiation may be carried out. Thereafter, for example, the above irradiated object can be processed into a desired stent shape by laser cutting or the like. For example, after a mixture containing the polymer and the crosslinking agent is molded into a tube shape by extrusion, injection molding, or the like and then the molded object is processed into a desired stent shape by laser cutting or the like, light irradiation may be carried out. For example, after a mixture containing the polymer and the crosslinking agent is processed into a stent shape by injection molding or the like, light irradiation may be carried out.

In the stent, in addition to the crosslinked polymer, other components may be contained without impairing exemplary effects of the present disclosure. For example, a drug that suppresses stenosis or obstruction of the vascular system which may occur when the stent is indwelled in a lesion area may be provided as an example of the other components. Specific examples of the drug include anticancer agents, immunosuppressive agents, antibiotics, antithrombotic agents, HMG-CoA reductase inhibitors, ACE inhibitors, calcium antagonists, antilipemic agents, integrin inhibitors, antiallergic agents, antioxidants, GPIIbIIIa antagonists, retinoids, lipid improvers, antiplatelet agents, and anti-inflammatory agents. For example, the drugs have an advantage that the drugs control behavior of tissue cells in a lesion area to be able to treat the lesion area. The other components described above may constitute the stent base body, together with the crosslinked polymer, or may be present as a coating layer on the stent base body having the crosslinked polymer.

Exemplary examples of the anticancer agent include, but not specifically limited to, paclitaxel, docetaxel, vinblastine, vindesine, irinotecan, pirarubicin, and the like.

Exemplary examples of the immunosuppressive agent include, but not specifically limited to, sirolimus derivatives, such as sirolimus, everolimus, pimecrolimus, and zotarolimus, biolimus (for example, Biolimus A9 (registered trademark)), tacrolimus, azathioprine, cyclosporine, cyclophosphamide, mycophenolate mofetil, gusperimus, and the like.

Exemplary examples of the antibiotic include, but not specifically limited to, mitomycin, adriamycin, doxorubicin, actinomycin, daunorubicin, idarubicin, pirarubicin, aclarubicin, epirubicin, zinostatin stimalamer, and the like.

Exemplary examples of the antithrombotic agent include, but not specifically limited to, aspirin, ticlopidine, argatroban, and the like.

Exemplary examples of the HMG-CoA reductase inhibitor include, but not specifically limited to, cerivastatin, cerivastatin sodium, atorvastatin, pitavastatin, fluvastatin, fluvastatin sodium, simvastatin, lovastatin, and the like.

Exemplary examples of the ACE inhibitor include, but not specifically limited to, quinapril, trandolapril, temocapril, delapril, enalapril maleate, captopril, and the like.

Exemplary examples of the calcium antagonist include, but not specifically limited to, hifedipine, nilvadipine, benidipine, nisoldipine, and the like.

An exemplary example of the antilipemic agent is, but not specifically limited to, probucol.

An exemplary example of the integrin inhibitor is, but not specifically limited to, AJM300.

An exemplary example of the antiallergic agent is, but not specifically limited to, tranilast.

Exemplary examples of the antioxidant include, but not specifically limited to, α-tocopherol, catechin, dibutylhydroxytoluene, and butylhydroxyanisole.

An exemplary example of the GPIIbIIIa antagonist is, but not specifically limited to, abciximab.

An exemplary example of the retinoid is, but not specifically limited to, all-trans retinoic acid.

An exemplary example of the lipid improver is, but not specifically limited to, eicosapentaenoic acid.

Exemplary examples of the antiplatelet agent include, but not specifically limited to, ticlopidine, cilostazol, and clopidogrel.

Exemplary examples of the anti-inflammatory agent include, but not specifically limited to, steroids such as dexamethasone and prednisolone.

For example, when the stent contains other components in addition to the crosslinked polymer, the crosslinked polymer is contained in an amount of 80% by weight or more, for example, 90% by weight or more, for example, 95% by weight or more (upper limit: 100% by weight) in total with respect to the whole stent, and the balance is the other components.

In an exemplary stent according to the present disclosure, in addition to the stent base body, a coating layer made of any biodegradable material may be provided on the stent base body without impairing the object and the effects of the present disclosure. An exemplary example of a biodegradable material used to form the coating layer is, but not specifically limited to, a polymer selected from a group consisting of polyesters, polyacid anhydrides, polycarbonates, polyphosphazenes, polyphosphoric acid esters, polypeptides, polysaccharides, proteins, and celluloses. More specific examples thereof include at least one or a blend of two or more selected from a group consisting of polylactic acids, polyglycolic acids, lactic acid-glycolic acid copolymers, polycaprolactones, lactic acid-caprolactone copolymers, polyhydroxybutyric acids, polymalic acids, poly-α-amino acids, collagen, laminin, heparan sulfate, fibronectin, vitronectin, chondroitin sulfate, and hyaluronic acids. Medically safe ones can be used in view of degradability in a living body. For example, the molecular weight, the degree of purification, the degree of crystallization of the biodegradable material which coats the outer surface of the stent (outer surface of the stent base body) are adjusted to suppress the hydrophilicity to a low level; and thereby, it is possible to increase the duration of maintaining the strength. For example, the degree of purification of the biodegradable material is increased to eliminate unreacted monomers and low molecular weight fractions, or the degree of crystallization is increased to suppress the amount of water infiltrating into the backbone of the stent; and thereby, for example, it is possible to increase the time of hydrolysis. In addition, the coating layer may also be a drug coating layer that contains the coating layer-forming biodegradable material and one or two or more of the above drugs at any ratio, for example, at a ratio of 1:99 to 99:1 (w/w), for example, 95:5 to 80:20 (w/w). A method for forming the coating layer is not specifically limited, and a general coating method can be applied similarly or after appropriately modified. For example, a method can be applied in which a biodegradable material and optionally the above drug and a suitable solvent are mixed to prepare a mixture, and the mixture is applied to the stent base body.

EXAMPLES

Exemplary effects of the present disclosure will be described using the following Examples and Comparative Examples. In Examples, "parts" or "%" may be used and, unless otherwise defined, represents "parts by weight" or "% by weight". In addition, unless otherwise specified, various operations are carried out at room temperature (25° C.).

Example 1

1 g of poly L-lactic acid (manufactured by BMG Inc., BioDegmer (registered trademark) PLLA, SP value: 23.1, weight average molecular weight: 510,000), 0.15 g of pentaerythritol tetraacrylate (SP value: 21.5, PETA) (manufactured by Sigma-Aldrich) as a crosslinking agent, 0.01 g of 2-hydroxy-1-[4-(2-hydroxyethoxy)phenyl]-2-methyl-1-propanone (Irgacure 2959, manufactured by BASF), and 29.6 g of chloroform were mixed to prepare a polymer solution.

The polymer solution was poured into a PFA petri dish with a diameter of 100 mm not to cause the mixing of air bubbles and was dried with air over one night at room temperature to obtain a cast film. The obtained film was irradiated with UV light of a wavelength of 365 nm from the front and back surfaces thereof using a UV irradiation device (VB-15201BY-A, manufactured by Ushio Inc.) such that the integral light quantity was 3,000 mJ/cm$^2$, to form a film (thickness: approximately 0.1 mm), and the film was peeled from the petri dish to obtain a test film.

Example 2

A test film was obtained in the same manner as in Example 1 except that the amount of the crosslinking agent was changed from 0.15 g to 0.2 g.

Example 3

A test film was obtained in the same manner as in Example 1 except that the amount of the crosslinking agent was changed from 0.15 g to 0.25 g.

Example 4

A test film was obtained in the same manner as in Example 1 except that the amount of the crosslinking agent was changed from 0.15 g to 0.3 g.

Example 5

A test film was obtained in the same manner as in Example 1 except that the amount of the crosslinking agent was changed from 0.15 g to 0.35 g.

Example 6

A test film was obtained in the same manner as in Example 2 except that 2-hydroxy-1-[4-(2-hydroxyethoxy)phenyl]-2-methyl-1-propanone as a polymerization initiator was not added and crosslinking was performed with an electron beam of 50 kGy.

Example 7

A test film was obtained in the same manner as in Example 4 except that 2-hydroxy-1-[4-(2-hydroxyethoxy)phenyl]-2-methyl-1-propanone as a polymerization initiator was not added and crosslinking was performed with an electron beam of 50 kGy.

Example 8

A test film was obtained in the same manner as in Example 2 except that the type of the crosslinking agent was changed from pentaerythritol tetraacrylate to dipentaerythritol penta/hexa-acrylate (SP value: 22.5) (manufactured by Sigma-Aldrich).

Example 9

A test film was obtained in the same manner as in Example 8 except that the amount of the crosslinking agent was changed from 0.2 g to 0.3 g.

Example 10

A test film was obtained in the same manner as in Example 2 except that the type of the crosslinking agent was changed from pentaerythritol tetraacrylate to ethylene glycol dimethacrylate (SP value: 18.2, EGDM) (manufactured by Sigma-Aldrich).

Example 11

A test film was obtained in the same manner as in Example 10 except that the amount of the crosslinking agent was changed from 0.2 g to 0.3 g.

Example 12

A test film was obtained in the same manner as in Example 2 except that the type of the crosslinking agent was changed from ethylene glycol dimethacrylate to triallyl isocyanate (SP value: 29.2, TAIC) (manufactured by Sigma-Aldrich).

Example 13

A test film was obtained in the same manner as in Example 12 except that the amount of the crosslinking agent was changed from 0.2 g to 0.3 g.

Example 14

A test film was obtained in the same manner as in Example 12 except that 2-hydroxy-1-[4-(2-hydroxyethoxy)phenyl]-2-methyl-1-propanone as a polymerization initiator was not added and crosslinking was performed with an electron beam of 50 kGy.

Example 15

A test film was obtained in the same manner as in Example 13 except that 2-hydroxy-1-[4-(2-hydroxyethoxy)phenyl]-2-methyl-1-propanone as a polymerization initiator was not added and crosslinking was performed with an electron beam of 50 kGy.

Example 16

A test film was obtained in the same manner as in Example 5 except that instead of polylactic acid, a copolymer of L-lactic acid and glycolic acid (Resomer (registered trademark) LG824S, manufactured by EVONIK Industries, SP value: 23.6, molecular weight: 360,000) was used.

Comparative Example 1

1 g of poly L-lactic acid (manufactured by BMG Inc., BioDegmer (registered trademark) PLLA, SP value: 23.1, weight average molecular weight: 510,000) and 29.6 g of chloroform were mixed to prepare a polymer solution. After the obtained polymer solution was poured into a PFA petri dish with a diameter of 100 mm not to cause the mixing of air bubbles and was dried with air at room temperature, the obtained polymer solution was dried under reduced pressure in a vacuum oven at 120° C. for 2 hours. The formed film (thickness: approximately 0.1 mm) was peeled from the PFA petri dish to obtain a test film.

Comparative Example 2

A test film was obtained in the same manner as in Example 1 except that the amount of the crosslinking agent was changed from 0.15 g to 0.1 g.

Comparative Example 3

A test film was obtained in the same manner as in Example 1 except that the amount of the crosslinking agent was changed from 0.15 g to 0.4 g.

Comparative Example 4

A test film was obtained in the same manner as in Example 8 except that the amount of the crosslinking agent was changed from 0.2 g to 0.4 g.

Comparative Example 5

1 g of a copolymer of L-lactic acid and glycolic acid (Resomer (registered trademark) LG824S, manufactured by EVONIK Industries, SP value: 23.6, molecular weight: 360,000) and 29.6 g of chloroform were mixed to prepare a polymer solution. After the obtained polymer solution was poured into a PFA petri dish with a diameter of 100 mm not to cause the mixing of air bubbles and was dried with air at room temperature, the obtained polymer solution was dried under reduced pressure in a vacuum oven at 120° C. for 2 hours. The formed film (thickness: approximately 0.1 mm) was peeled from the PFA petri dish to obtain a test film.

[Evaluation]

<Young's Modulus>

A 5B-type dumbbell test piece was fabricated according to ISO 527-2 with a punching die and then was subjected to a tensile test under an atmosphere of 37° C. at a distance of 20 mm between chucks and a test speed of 1 mm/min using a tensile tester equipped with a thermostatic chamber (Autograph AG-1kNIS, manufactured by Shimadzu Corporation), and the Young's modulus was determined from an initial slope in an elastic deformation area of the stress-strain curve.

<Recovery Rate after 10 Seconds and Recovery Rate after 20 Minutes>

A 5B-type dumbbell test piece was fabricated according to ISO 527-2 with a punching die and then subjected to two cycles of a tensile test under an atmosphere of 37° C., as illustrated in FIG. 2, at a distance of 20 mm between chucks, a test speed of 10 mm/min, a maximum tensile distance of 0.6 mm (length of a parallel part of the dumbbell test piece: 12 mm×5%), and a tensile strain-retention time of 10 seconds using the tensile tester equipped with a thermostatic chamber (Autograph AG-1kNIS, manufactured by Shimadzu Corporation), and as illustrated in FIG. 3, the recovery rate was calculated as a ratio (($x_2/x_1$)×100%) of an elongation distance $x_2$ in a second cycle (distance from a stress-detected position to the maximum tensile position in the second cycle) to an elongation distance $x_1$ in a first cycle (distance from a stress-detected position to the maximum tensile position in the first cycle). Note that the stand-by time between cycles was set to 10 seconds or 20 minutes.

The recovery rate measured in this test correlates to the degree of the shape recovery of the stent. When the stent is restricted by an external force to be contracted in diameter, a strain in the tensile direction is generated on an outer curving side of an apex of the bent portion. When the restriction in this state is released, since a reduction in strain occurs as seen in this test, the diameter of the stent returns to the diameter before contraction in diameter. In this case, the higher the recovery rate, the more the strain is reduced, and thus the diameter of the stent becomes closer to the diameter before contraction in diameter. Namely, the recovery rate correlates to the degree of shape recovery, and the higher the recovery rate, the higher the degree of shape recovery.

<Strain-Resistance Properties>

A 5B-type dumbbell test piece was fabricated according to ISO 527-2 with a punching die and then was subjected to a tensile test under an atmosphere of 37° C. at a distance of 20 mm between chucks and a test speed of 10 mm/min using the tensile tester equipped with a thermostatic chamber (Autograph AG-1kNIS, manufactured by Shimadzu Corporation), and it was confirmed whether or not the sample was fractured when the test piece was pulled by 1.2 mm (length of a parallel part of the dumbbell test piece: 12 mm×10%). A sample without fracture was rated as o, and a sample with fracture was rated as x.

In a diameter-decreased state, in the vicinity of the apex of the bent, the outer curving side was stretched, namely, was subjected to a strain in the tensile direction, and an inner curving side was compressed, namely, was subjected to a strain in a compression direction. Here, the strain-resistance properties of the stent were evaluated from whether or not fracture occurred when a strain in the tensile direction was applied. Note that a product designed as a self-expandable stent has a tensile strain of approximately 10% on the outer curving side or a compression strain of approximately 10% on the inner curving side in a diameter-decreased state, and thus regarding the strain-resistance properties, the stent that is fractured at a strain of 10% has a possibility of undergoing fracture in a diameter-decreasing operation.

<Martens Hardness Test>

According to ISO 14577-1 "Instrumented indentation hardness", a sheet surface was subjected to an indenter indentation test using a dynamic ultra-micro hardness tester (DUH-W201S, manufactured by Shimadzu Corporation) under the following conditions: indenter: Berkovich indenter of a regular triangular pyramid shape with an intercristal angle of 115 (made of diamond), test force: 10 mN, loading rate: 0.473988 mN/sec, and retention time: 5 seconds, to obtain the indentation depth (μm) in this case, and the Martens hardness was determined based on the formula: [Martens hardness $(N/mm^2)$]=1,000×[load at indentation depth (mN)]/26.43×[indentation depth (μm)]2.

<Gel Fraction>

Approximately 25 mg of each film was precisely weighed and was immersed in 25 ml of chloroform at 25° C. for 3 hours, followed by filtration with a 200-mesh stainless wire net, and an insoluble matter having a wire net shape was dried in vacuum. Next, the weight of the insoluble matter was precisely weighed and the gel fraction was calculated in percentage according to the following formula.

Gel fraction (%)={weight of insoluble matter (mg)/weight of weighed film (mg)}×100

<Biodegradability Test>

A 5B-type dumbbell test piece was fabricated according to ISO 527-2 with a punching die, 50 mL of a phosphate buffer saline solution (pH 7.4) was put into a sample bottle of 50 mL, and then the dumbbell test piece was put in to be completely immersed therein. The sample bottle was put in and placed in an oven at 50° C. for 2 weeks. The sample was taken out from the phosphate buffer saline solution and was immersed in ion exchange water at 37° C. to wash the sample. Thereafter, the sample was quickly subjected to a tensile test under an atmosphere of 37° C. at a distance of 20 mm between chucks and a test speed of 10 mm/min using the tensile tester equipped with a thermostatic chamber (Autograph AG-1kNIS, manufactured by Shimadzu Corporation) to measure the elongation at fracture. In addition, separately, as a test specimen before hydrolysis, a sample immersed in the ion exchange water at 37° C. for 2 hours was taken out to be quickly subjected to a tensile test. Finally, the ratio of the elongation at fracture after a hydrolysis test to the elongation at fracture before hydrolysis ((elongation at fracture after hydrolysis test/elongation at fracture before hydrolysis)×100(%)) was determined.

The following Table 1 shows polymer solution compositions and evaluation results of the above evaluation in Examples and Comparative Examples. The gel fraction in each of Examples was 50% or more. For example, the gel fraction was 97% in Example 1, 96% in Example 2, 90% in Example 6, 79% in Example 9, and 93% in Example 10. Furthermore, all of Examples exhibit biodegradability. For example, in Example 3, the elongation at fracture before hydrolysis test was 11.8%, the elongation at fracture after hydrolysis test was 3.2%, and the ratio of the elongation at fracture after hydrolysis test to the elongation at fracture before hydrolysis was 27.1%.

TABLE 1

|  |  | Example | | | | | | | | |
|---|---|---|---|---|---|---|---|---|---|---|
|  |  | 1 | 2 | 3 | 4 | 5 | 6 | 7 | 8 | 9 |
| Polymer | Type | PLLA | | | | | | | | |
|  | SP value | 23.1 | 23.1 | 23.1 | 23.1 | 23.1 | 23.1 | 23.1 | 23.1 | 23.1 |
|  | Molecular weight (Mw) | 510,000 | 510,000 | 510,000 | 510,000 | 510,000 | 510,000 | 510,000 | 510,000 | 510,000 |
|  | Weight | 1 g | 1 g | 1 g | 1 g | 1 g | 1 g | 1 g | 1 g | 1 g |
| Cross-linking agent | Type | | | | PETA | | | | dipentaerythritol penta/hexa-acrylate | |
|  | SP value | 21.5 | 21.5 | 21.5 | 21.5 | 21.5 | 21.5 | 21.5 | 22.5 | 22.5 |
|  | SP value difference *1 | 1.6 | 1.6 | 1.6 | 1.6 | 1.6 | 1.6 | 1.6 | 0.6 | 0.6 |

TABLE 1-continued

|  |  |  |  |  |  |  |  |  |  |
|---|---|---|---|---|---|---|---|---|---|
| Weight | 0.15 g | 0.2 g | 0.25 g | 0.3 g | 0.35 g | 0.2 g | 0.3 g | 0.2 g | 0.3 g |
| Ratio of weight of crosslinking agent to weight of polymer (%) | 15% | 20% | 25% | 30% | 35% | 20% | 30% | 20% | 30% |
| Weight of photopolymerization initiator | 0.01 g | 0.01 g | 0.01 g | 0.01 g | 0.01 g | — | — | 0.01 g | 0.01 g |
| Young's modulus (MPa) | 1,958 | 2,081 | 2,005 | 1,976 | 1,959 | 1,850 | 1,828 | 2,378 | 2,246 |
| Recovery rate after 10 seconds (%) | 71 | 71 | 83 | 80 | 87 | 70 | 71 | 77 | 83 |
| Recovery rate after 20 minutes (%) | 82 | 100 | 98 | 95 | 95 | — | — | — | — |
| Strain-resistance properties | ○ | ○ | ○ | ○ | ○ | ○ | ○ | ○ | ○ |
| Martens hardness (N/mm$^2$) | 171 | 182 | 183 | 184 | 169 | 160 | 202 | 255 | 230 |

|  |  |  | Example |  |  |  |  |  |  |
|---|---|---|---|---|---|---|---|---|---|
|  |  |  | 10 | 11 | 12 | 13 | 14 | 15 | 16 |
| Polymer | Type |  | PLLA |  |  |  |  |  | PLLA-co-PGA |
|  | SP value |  | 23.1 | 23.1 | 23.1 | 23.1 | 23.1 | 23.1 | 23.6 |
|  | Molecular weight (Mw) |  | 510,000 | 510,000 | 510,000 | 510,000 | 510,000 | 510,000 | 360,000 |
|  | Weight |  | 1 g | 1 g | 1 g | 1 g | 1 g | 1 g | 1 g |
| Cross-linking agent | Type |  | EGDM |  | TAIC |  |  |  | PETA |
|  | SP value |  | 18.2 | 18.2 | 29.2 | 29.2 | 29.2 | 29.2 | 21.5 |
|  | SP value difference *1 |  | 4.9 | 4.9 | 6.1 | 6.1 | 6.1 | 6.1 | 2.1 |
|  | Weight |  | 0.2 g | 0.3 g | 0.2 g | 0.3 g | 0.2 g | 0.3 g | 0.35 g |
| Ratio of weight of crosslinking agent to weight of polymer (%) |  |  | 20% | 30% | 20% | 30% | 20% | 30% | 35% |
| Weight of photopolymerization initiator |  |  | 0.01 g | 0.01 g | 0.01 g | 0.01 g | — | — | 0.01 g |
| Young's modulus (MPa) |  |  | 2,552 | 2,325 | 2,166 | 2,194 | 1,102 | 819 | 2,242 |
| Recovery rate after 10 seconds (%) |  |  | 70 | 76 | 70 | 71 | 70 | 71 | 70 |
| Recovery rate after 20 minutes (%) |  |  | — | — | — | — | — | — | — |
| Strain-resistance properties |  |  | ○ | ○ | ○ | ○ | ○ | ○ | ○ |
| Martens hardness (N/mm$^2$) |  |  | 254 | 237 | 200 | 199 | 123 | 107 | 222 |

|  |  |  | Comparative Example |  |  |  |  |
|---|---|---|---|---|---|---|---|
|  |  |  | 1 | 2 | 3 | 4 | 5 |
| Polymer | Type |  | PLLA |  |  |  | PLLA-co-PGA |
|  | SP value |  | 23.1 | 23.1 | 23.1 | 23.1 | 23.6 |
|  | Molecular weight (Mw) |  | 510,000 | 510,000 | 510,000 | 510,000 | 360,000 |
|  | Weight |  | 1 g | 1 g | 1 g | 1 g | 1 g |
| Cross-linking agent | Type |  | — | PETA | PETA | dipentaerythritol penta/hexa-acrylate | — |
|  | SP value |  | — | 21.5 | 21.5 | 22.5 | — |
|  | SP value difference *1 |  | — | 1.6 | 1.6 | 0.6 | — |
|  | Weight |  | — | 0.1 g | 0.4 g | 0.4 g | — |
| Ratio of weight of crosslinking agent to weight of polymer (%) |  |  | — | 10% | 40% | 40% | — |
| Weight of photopolymerization initiator |  |  | — | 0.01 g | 0.01 g | 0.01 g | — |

TABLE 1-continued

|  |  |  |  |  |  |
|---|---|---|---|---|---|
| Young's modulus (MPa) | 2,127 | 1,958 | 1,963 | 2,019 | 2,061 |
| Recovery rate after 10 seconds (%) | 57 | 60 | 88 | 81 | 61 |
| Recovery rate after 20 minutes (%) | 75 | — | — | — | — |
| Strain-resistance properties | ○ | x | x | x | x |
| Martens hardness (N/mm$^2$) | 192 | 163 | 204 | 218 | 202 |

*1 difference (absolute value) between the solubility parameter value of the crosslinking agent and the solubility parameter value of the constitutional unit (A)

As can be seen from the above results, in the crosslinked polymers of Examples, the Young's modulus were high, the strain-resistance properties were good, and the recovery rates after 10 seconds were high.

On the other hand, in Comparative Example 1 where polylactic acid was used with no crosslinking agent added and in Comparative Example 5 where a copolymer of lactic acid and glycolic acid was used with no crosslinking agent added, the Young's modulus were high, but the recovery rates were low and the strain-resistance properties were also inferior. In addition, in Comparative Example 2 where the amount of addition of the crosslinking agent was 10% by weight with respect to the amount of the polylactic acid, the recovery rate after 10 seconds was remarkably lower than those in Examples. In Comparative Examples 3 and 4 where the amount of addition of the crosslinking agent was 40% by weight with respect to the amount of polylactic acid, the strain-resistance properties were remarkably reduced.

From the above results, it is found that since the content of the constitutional unit (B) obtained from the crosslinking agent is 15% by weight to 35% by weight with respect to the content of the constitutional unit (A), while maintaining a sufficient radial force, the stent has a high speed of shape recovery when the stent is released from restriction in a contracted state, and has sufficient resistance to a local stress to the stent strut, the local stress being generated when the stent is contracted in diameter from an expanded state to a crimped state (contracted state).

Note that the recovery rates after 20 minutes in Examples 6 to 16 were 70% or more.

Example 17 and Comparative Example 6

A tube was fabricated from a material of Example 4 or Comparative Example 1, and then into a self-expandable stent by laser cutting (thickness: 150 μm, strut width: 150 μm, outer diameter: 3.5 mm (D1), length: 18 mm) (stent fabricated in Example 4: Example 17, stent fabricated in Comparative Example 1: Comparative Example 6).

The fabricated self-expandable stent was contracted in diameter and was inserted into a PTFE tube having an inner diameter of 1.2 mm. The tube was immersed in ion exchange water of which the temperature was controlled at 37° C., and the inserted self-expandable stent was released from the tube and was allowed to stand still in the ion exchange water at 37° C. for 1 minute. Thereafter, the stent was taken out from the water and the outer diameter (D2) of the stent was measured again with a caliper to calculate the shape recovery rate ((D2/D1)×100(%)).

As a result, the shape recovery rate in Example 17 was 90%, and the shape recovery rate in Comparative Example 6 was 46%.

In addition, the radial force was measured according to ASTM F3067-14 using the self-expandable stent.

(Measurement Conditions)

Measurement apparatus: Radial Force Testing System-Model RFJ manufactured by Blockwise Engineering LLC Measurement temperature: 37° C.

Speed (rate of diameter): 0.05 mm/sec

Measurement diameter: 3.2 mm to 1.5 mm

Measurement procedure: a sample is set in the apparatus heated to 37° C. The radial force was measured when the diameter is decreased to 3.2 mm to 1.5 mm at a speed of 0.05 mm/sec and successively increased to 1.5 mm to 3.2 mm.

The result is shown in FIG. 4. Accordingly, it is found that the stent of Example 17 exhibits good shape recoverability while maintaining a high radial force.

This application is based on Japanese Patent Application No. 2018-048377, filed on Mar. 15, 2018, the content of which is incorporated herein by reference in its entity.

REFERENCE SIGNS LIST

3 First wave strut
4 Second wave strut
5 Connection strut
6 Joint portion
7 Radiopaque marker
8 Bulging portion
9, 51 Bent portion
10 Stent
30 Stent base body
35a, 45a Slightly-bent portion
38 Top point of first wave strut 3
39 Bottom point of first wave strut 3
48 Bottom point of second wave strut 4
49 Top point of second wave strut 4

What is claimed is:

1. A self-expandable stent comprising a crosslinked polymer consisting of a constitutional unit (A) obtained from a monomer that constitutes a rigid biodegradable polymer when homopolymerized and a constitutional unit (B) obtained from a crosslinking agent,
wherein a content of the constitutional unit (B) is 15% by weight to 35% by weight with respect to a content of the constitutional unit (A),
wherein the crosslinking agent is a monomer having two or more polymerizable unsaturated bonds, wherein the crosslinking agent includes pentaerythritol tetraacrylate, dipentaerythritol penta/hexa-acrylate, or a combination thereof.

2. The self-expandable stent according to claim 1, wherein a Young's modulus of the crosslinked polymer is 500 N/mm$^2$ or more and a recovery rate thereof after 10 seconds is 65% or more.

3. The self-expandable stent according to claim 1, wherein a Martens hardness of the crosslinked polymer is 50 N/mm$^2$ or more in a case where a loading-unloading test is carried out using a nanoindenter.

4. The self-expandable stent according to claim 1, wherein the crosslinked polymer is obtained by polymerizing the crosslinking agent with a polymer containing the constitutional unit (A) obtained from the monomer that constitutes the rigid biodegradable polymer when homopolymerized and, an absolute value of a difference between a solubility parameter value of the crosslinking agent and a solubility parameter value of the monomer that constitutes the rigid biodegradable polymer when homopolymerized is 5 (J/cm$^3$)$^{1/2}$ or less.

5. The self-expandable stent according to claim 1, wherein the monomer that constitutes the rigid biodegradable polymer when homopolymerized contains at least one of lactic acid and glycolic acid.

6. The self-expandable stent according to claim 1, wherein the content of the constitutional unit (B) is 25% by weight to 35% by weight with respect to the content of the constitutional unit (A).

7. The self-expandable stent according to claim 1, wherein the monomer that constitutes the rigid biodegradable polymer when homopolymerized includes lactic acid, glycolic acid, or a combination thereof.

8. The self-expandable stent according to claim 1, wherein the monomer that constitutes the rigid biodegradable polymer when homopolymerized includes poly L-lactic acid.

9. A method for producing a self-expandable stent, the method comprising:

polymerizing a polymer consisting of a constitutional unit (A) obtained from a monomer that constitutes a rigid biodegradable polymer when homopolymerized and a constitutional unit (B) obtained from a crosslinking agent having a content of 15% by weight to 35% by weight with respect to a content of the constitutional unit (A) to obtain a crosslinked polymer, wherein the crosslinking agent is a monomer having two or more polymerizable unsaturated bonds, wherein the crosslinking agent includes pentaerythritol tetraacrylate, dipentaerythritol penta/hexa-acrylate, or a combination thereof; and producing the stent using the crosslinked polymer.

10. The method for producing a self-expandable stent according to claim 9, wherein a weight average molecular weight of the polymer is 100,000 to 1,000,000.

11. The method for producing a self-expandable stent according to claim 9, wherein the polymer and the crosslinking agent are polymerized under irradiation with an ultraviolet ray.

12. The method for producing a self-expandable stent according to claim 9, wherein the polymer containing the constitutional unit (A) and the crosslinking agent are polymerized in the presence of a photopolymerization initiator.

13. The method for producing a self-expandable stent according to claim 9, wherein the monomer that constitutes the rigid biodegradable polymer when homopolymerized includes lactic acid, glycolic acid, or a combination thereof.

14. The method for producing a self-expandable stent according to claim 9, wherein the monomer that constitutes the rigid biodegradable polymer when homopolymerized includes poly L-lactic acid.

15. The self-expandable stent according to claim 1, wherein the crosslinking agent is pentaerythritol tetraacrylate.

16. The method for producing a self-expandable stent according to claim 9, wherein the crosslinking agent is pentaerythritol tetraacrylate.

\* \* \* \* \*